(12) United States Patent
El Saddik et al.

(10) Patent No.: US 9,699,182 B2
(45) Date of Patent: Jul. 4, 2017

(54) ELECTROCARDIOGRAM (ECG) BIOMETRIC AUTHENTICATION

(71) Applicants: Abdulmotaleb El Saddik, Ottawa (CA); Juan Sebastian Arteaga Falconi, Ottawa (CA); Hussein Al Osman, Ottawa (CA)

(72) Inventors: Abdulmotaleb El Saddik, Ottawa (CA); Juan Sebastian Arteaga Falconi, Ottawa (CA); Hussein Al Osman, Ottawa (CA)

( * ) Notice: Subject to any disclaimer, the term of this patent is extended or adjusted under 35 U.S.C. 154(b) by 0 days.

(21) Appl. No.: 14/748,913

(22) Filed: Jun. 24, 2015

(65) Prior Publication Data

US 2015/0373019 A1    Dec. 24, 2015

Related U.S. Application Data

(60) Provisional application No. 62/016,444, filed on Jun. 24, 2014.

(51) Int. Cl.
| | | |
|---|---|---|
| G06F 21/00 | (2013.01) | |
| G06F 21/32 | (2013.01) | |
| G06K 9/00 | (2006.01) | |
| H04L 29/06 | (2006.01) | |
| H04W 12/08 | (2009.01) | |
| A61B 5/117 | (2016.01) | |
| H04W 12/06 | (2009.01) | |
| A61B 5/0452 | (2006.01) | |

(52) U.S. Cl.
CPC ........ *H04L 63/0861* (2013.01); *A61B 5/0452* (2013.01); *A61B 5/117* (2013.01); *G06F 21/00* (2013.01); *G06F 21/32* (2013.01); *H04W 12/06* (2013.01)

(58) Field of Classification Search
CPC .... G06F 21/00; G06F 21/32; G06K 9/00; H04L 29/06; H04W 12/08
USPC ...... 340/5.52, 5.53, 5.8, 5.81, 5.83; 382/115, 382/173; 707/100
See application file for complete search history.

(56) References Cited

U.S. PATENT DOCUMENTS 6,483,929 B1 * 11/2002 Murakami ......... G06K 9/00496
340/5.83
7,617,058 B2 * 11/2009 Kim .................. G06K 9/00885
702/79

(Continued)

OTHER PUBLICATIONS

L. Biel, O. Pettersson, L. Philipson and P. Wide, "Ecg analysis: a new approach in human identification," Instrumentation and Measurement, IEEE Transactions on, vol. 50, No. 3, pp. 808-812, 2001.
S. A. Israel, J. M. Irvine, A. Cheng, M. D. Wiederhold and B. K. Wiederhold, "ECG to identify individuals," Pattern Recognition, vol. 38, No. 1, pp. 133-142, 2005.
R. Frischholz and U. Dieckmann, "BioID: a multimodal biometric identification system," Computer, vol. 33, No. 2, pp.54-68, Feb. 2000.
S. Liu and M. Silverman, "A Practical Guide to Biometric Security Technology," IT Professional, vol. 3, No. 1, pp. 27-32, Jan. 2001.
S. K. Dahel and Q. Xiao, "Accuracy performance analysis of multimodal biometrics," In Information Assurance Workshop, 2003. IEEE Systems, Man and Cybemetrics Society, 2003.

(Continued)

*Primary Examiner* — Nam V Nguyen
(74) *Attorney, Agent, or Firm* — Gowling WLG (Canada) LLP

(57) ABSTRACT

Electrocardiogram, better known as ECG or EKG, is a method used to measure and record the electrical potential generated by the heart on the skin. ECG data is unique to a user and can be used for authentication systems such as access or financial cards or for granting access to computing devices such as mobile devices. Electrode contact on a card or device are used to received ECG data which is processed to extract features of the ECG which are compared to a template for a user.

17 Claims, 17 Drawing Sheets

(56) References Cited

U.S. PATENT DOCUMENTS

| | | | |
|---|---|---|---|
| 7,689,833 B2* | 3/2010 | Lange | A61B 5/04525 |
| | | | 382/115 |
| 8,301,232 B2 | 10/2012 | Albert et al. | |
| 8,489,181 B1* | 7/2013 | Schipper | A61B 5/04011 |
| | | | 600/509 |
| 8,886,316 B1* | 11/2014 | Juels | A61N 1/37252 |
| | | | 607/30 |
| 8,902,045 B1* | 12/2014 | Linn | G06F 21/32 |
| | | | 340/5.53 |
| 8,922,342 B1* | 12/2014 | Ashenfelter | G07C 9/00087 |
| | | | 340/5.52 |
| 8,924,736 B1* | 12/2014 | Dusan | G06F 21/32 |
| | | | 340/5.52 |
| 9,119,539 B1* | 9/2015 | Dotan | A61B 5/02438 |
| 2003/0060689 A1* | 3/2003 | Kohls | A61B 5/0002 |
| | | | 600/300 |
| 2005/0177049 A1* | 8/2005 | Hardahl | A61B 5/0452 |
| | | | 600/509 |
| 2010/0090798 A1* | 4/2010 | Garcia Molina | G06K 9/0055 |
| | | | 340/5.53 |
| 2014/0165184 A1* | 6/2014 | Lange | G06F 21/32 |
| | | | 726/19 |
| 2014/0188770 A1* | 7/2014 | Agrafioti | A61B 5/117 |
| | | | 706/13 |

OTHER PUBLICATIONS

B.-U. Kohler, C. Flennig and R. Orglmeister, "The principles of software QRS detection," Engineering in Medicine and Biology Magazine, IEEE, vol. 21, No. 1, pp. 42-57, Jan. 2002.

* cited by examiner

ELECTROCARDIOGRAM (ECG) BIOMETRIC AUTHENTICATION

TECHNICAL FIELD

The present disclosure relates to biometric authentication and in particular to biometric authentication on cards and mobile devices.

BACKGROUND

Biometric technologies offer better security mechanisms over traditional authentication methods, like password based ones, given the fact that the biometric feature is a unique physiological characteristic that is always present and, depending on the method used, may not be visible to other people. However, one concern is that some biometric techniques have certain hardware and response time requirements that make them inappropriate for mobile devices and cards.

Fingerprint is a popular biometric technique and has been used for over 100 years in different applications, including authentication on mobile phones. But fingerprint authentication can fail if the fingerprint is damaged or, in a worst case scenario, spoofed by an attacker that captures the prints left by users on objects. This vulnerability has been demonstrated with commercial mobile phones that use fingerprints.

Electrocardiogram (referred to as ECG or EKG) methods have the advantage of concealing the biometric features during authentication. However, complex hardware is required to acquire this signal, making it hard to implement in mobile devices. Current ECG authentication algorithms are not designed to work in mobile environments given the fact that they require lengthy ECG signals or need to be combined with other biometric methods in order to achieve satisfactory results.

The use of cards for financial transactions or secure access has become indispensable in the last few decades. This popularity has also been accompanied by security concerns. Traditional cards do not support biometric authentication and therefore are not explicitly associated with their owner. Financial institutions have tried to address this problem through the introduction of PINs (Personal Verification Numbers) and integrated circuits on cards. These features remain only useful for contact cards (the type that is inserted into readers). This has decreased the number of breaches, but passive attacks (PIN theft or signature forging) are still problematic.

Mobile devices such as smart phones have become indispensable gadgets for numerous functions. Users are becoming more comfortable with the idea of storing highly private information such as emails, photos, and other sensitive documents on such devices. The popular mobile login methods rely on numerical or graphical passwords. These techniques are vulnerable to passive attacks instigated by individuals watching from a short distance in order to see the phone screen or the movement of the fingers with the goal of stealing the password.

Accordingly, systems and methods that enable biometric authentication on cards or mobile devices remain highly desirable.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
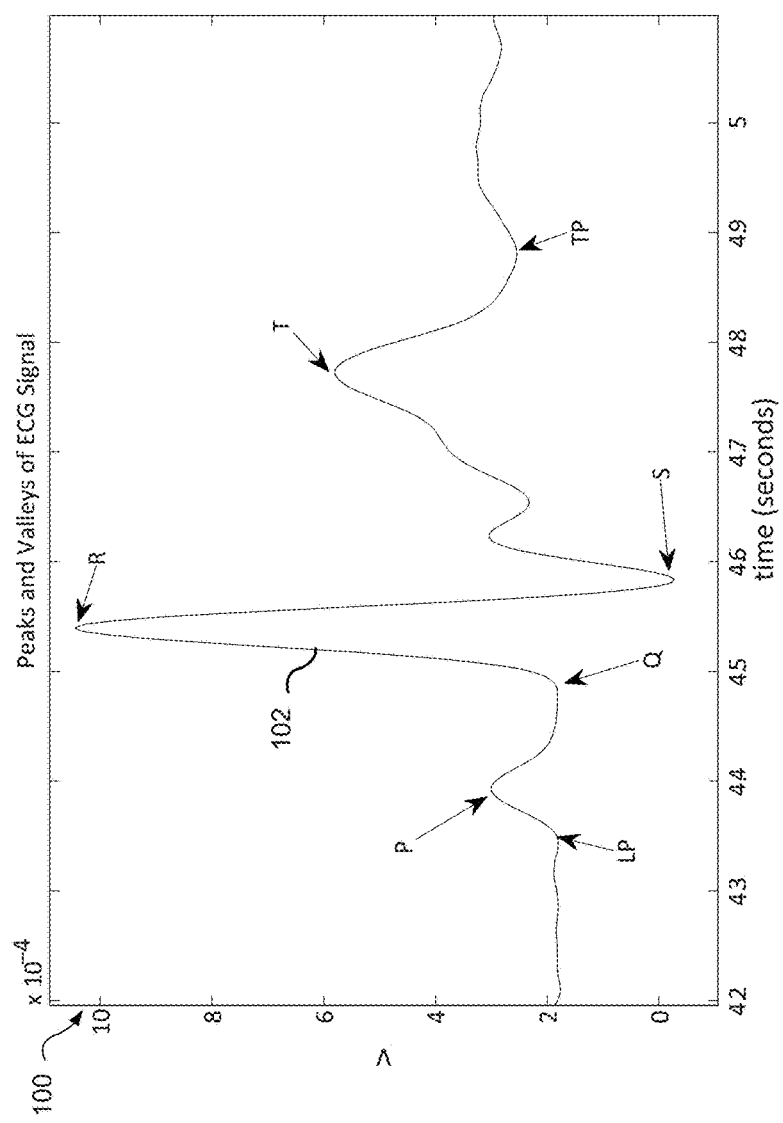
FIG. 1 shows an ECG heartbeat.

Embodiments are described below; by way of example only, with reference to FIGS. 1-17.

In accordance with an aspect of the present disclosure there is provided a method of security authentication, the method comprising: receiving electrocardiogram (ECG) signals from contact electrodes; transferring ECG signals to a processor; extracting features from ECG data of the ECG signal by the processor; verifying ECG data against stored biometric information template (BIT) associated with a user; and providing access to the user based upon confirmed ECG data.

In accordance with another aspect of the present disclosure there is provided an electrocardiogram (ECG) authentication device comprising: at least two electrodes; a microcontroller coupled to the electrodes for processing an ECG signal received from the electrodes; and memory containing instructions for processing the ECG signal by the microcontroller to extract features from ECG data which is verified against a stored biometric information template (BIT) whereby access is granted to the device or a computing system interfaced with the ECG device based upon comparison of the ECG data to the BIT wherein the BIT is associated with a user of the ECG device.

In accordance with an aspect of the present disclosure there is provided a non-transitory computer readable memory containing instruction thereon which when executed by a processor for providing security authentication by receiving electrocardiogram (ECG) signals from contact electrodes; transferring ECG signals to a processor; extracting features from ECG data of the ECG signal by the processor; verifying ECG data against stored biometric information template (BIT) associated with a user; and providing access to the user based upon confirmed ECG data.

Electrocardiogram, better known as ECG, is a method used to measure and record the electrical potential generated by the heart on the skin. An ECG heartbeat 102 is shown in a graph 100 of FIG. 1 and has three main complexes: P, QRS, and T where The P wave represents the start of electrical depolarization of the sinus node and the sequential right and left atrial contraction, the QRS complex signifies the electrical depolarization of the right and left ventricles, and the T wave corresponds to the electrical repolarization of the ventricles. The Q, R, and S waves occur in rapid succession, and reflect a single event, and thus are usually considered together as the QRS complex. A Q wave is any downward deflection after the P wave. An R wave follows as an upward deflection, and the S wave is any downward deflection after the R wave and the T wave follows the S wave. The sensor that measures this signal is called the electrocardiograph; it captures the information by means of conductive electrodes placed on the surface of the arms, legs, and chest wall This present disclosure provides an electronic contact or contactless identification card with an Electrocardiography (ECG) biometric security feature. The method implemented for providing biometric security can also be utilized in mobile devices for providing user authentication. The card can be used for financial transactions (debit or credit) or secure access. It is fitted with two or more electrodes made from conductive material and an integrated circuit. The card holder must place a right hand finger and a left hand finger in a predefined configuration on the electrodes to trigger the authentication operation. This process serves as a replacement or accompaniment to PIN (Personal Verification Number) based card authentication. The card can supply its biometric information to a reader in compliance with existing standards such as ISO/IEC 7816 and ISO/IEC 14443. Such biometric method is ideal for cards since ECG circuitry can be inserted into its confines. Conversely, other popular biometric methods' circuitry and sensors, such as that of fingerprint readers, cannot be fitted onto a card.

The disclosure uses ECG biometric authentication for financial or access cards. This mechanism can replace or complement the PIN based authentication. Also, stolen access cards cannot be used by anyone other than their authorized user. Financial cards can be equipped with electrodes that indicate the type of account associated with a particular transaction. In the physical design of the card, several electrode placements are possible. For example, they can be placed on the top, bottom, side or reverse side of the card. The ECG biometric authentication may also be used for security access or verification system such as access control entry system, identity verification systems or mobile devices. Additional biometric data may also be used to verify identity such as iris or fingerprints to supplement ECG data.

Figure 2:
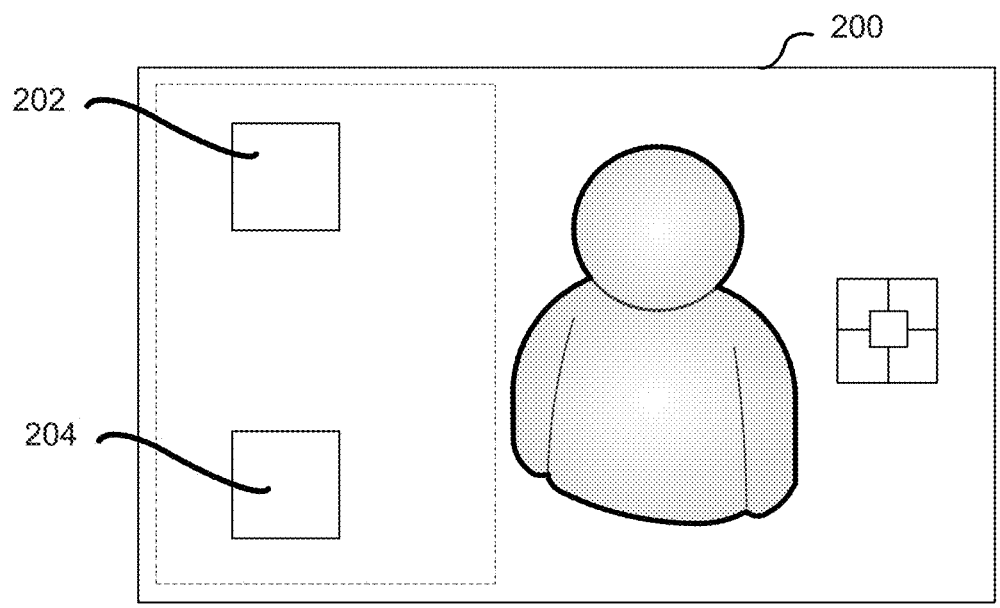
FIG. 2 shows a representation of ECG electrodes on card.

As shown in FIG. 2, the card 200 has ECG circuitry embedded between its layers. Two or more electrodes 202, 204 are fitted onto the card 200. The electrodes are made from metal or any other conductive materials placed on the extremities of the card so that they can be easily clutched by the thumbs (or other fingers) on both hands. Other ergonomic electrode placements are also possible.

Figure 3:
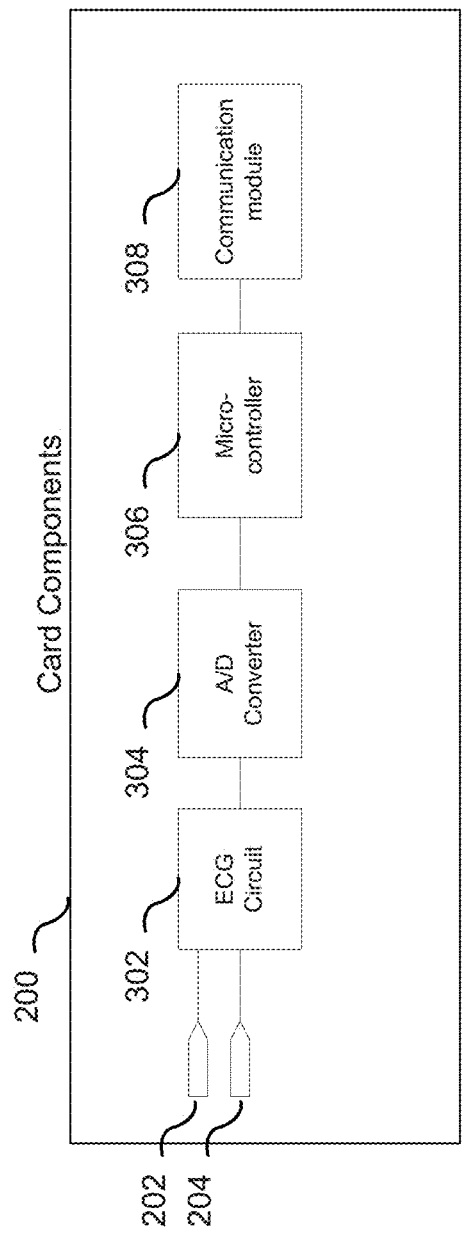
FIG. 3 shows a representation of card components.

Referring to FIG. 3, the electrodes are connected to the circuitry 202 that is responsible for filtering and amplifying the electrical current collected by the electrodes. The circuitry can include safety mechanisms to prevent reverse flow or damage to the electronic components. An analog to digital (A/D) converter 304 then digitizes the processed electrical signal and forwards it to a microcontroller 306. The microcontroller 308 prepares the data (or selected portions of it) to be sent through various mediums to the reader.

Figure 4:
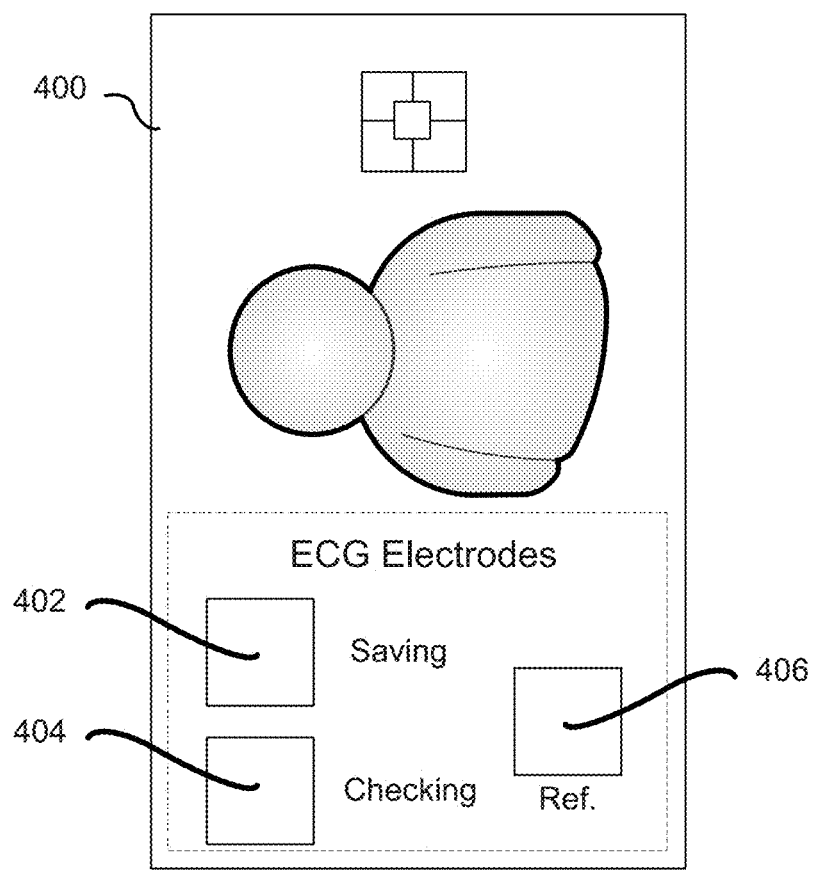
FIG. 4 shows an example of a financial card fitted with three electrodes.

FIG. 4 shows an example of a financial card 400 fitted with three electrodes 402-406. The electrode on the right side, referred to as the "Reference" is touched by a right hand finger. Each of the electrodes on the left side is associated with a type of account the transaction should be applied to ("Saving" or "Checking"). The user must touch one of them with a left hand finger in order to perform a transaction on the corresponding account type.

The card communicates with a reader in one of three modes:

Contact Mode:
refers to direct physical contact with the reader's circuitry and requires the insertion of the card into the reader.

Contactless Mode:
implies wireless communication with the reader on a licensed or unlicensed radio band. Can be RFID but not limited to it.

Figure 5:
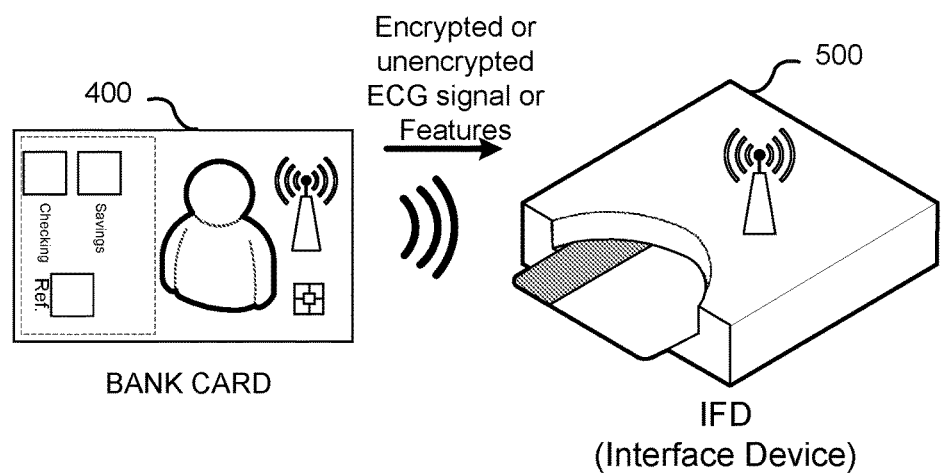
FIG. 5 shows a card in contact and contactless mode.

Contact and Contactless Mode:
indicates support and possible simultaneous use of both modes of communication as shown in FIG. 5 where the reader 500 may communicate wirelessly or require insertion of the card 400.

In any of the cases presented above, the card complies with existing standards for contact and contactless financial and access cards. Nonetheless, the authentication operation can take place on the reader or the financial institution's servers. For reasons of abstraction, the aforementioned servers are referred to as Financial Cloud (FC) but other terms may be utilized. These two approaches are described in the following sections.

On-Reader Authentication—

In this approach the ECG authentication process is achieved locally on the reader. This approach can be further divided into two modes, as described below.

Contact Mode with On-Reader Authentication—

Figure 6:
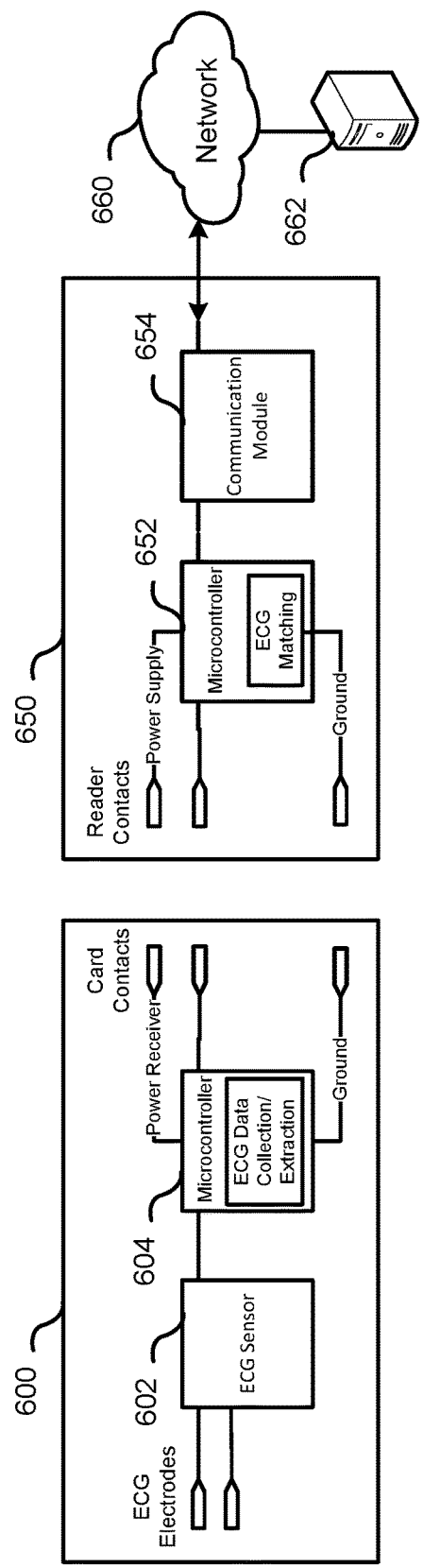
FIG. 6 shows contact mode with on-reader authentication.

The components required for the Contact Mode with On Reader Authentication are shown in FIG. 6. The ECG circuitry is directly powered by the reader. The microcontroller 604 on the card 600 collects and extracts the relevant ECG data from ECG sensor 602 and forwards it through a physical connection to the reader 650. The microcontroller 652 or processor 652 of the reader 602 then queries the server 662 via a network 660 via communication module 654 to obtain the stored Biometric information Template (BIT) for a particular card holder. The reader can then run a matching algorithm to compare the received ECG data to the BIT.

Contactless Mode with On-Reader Authentication—

Figure 7:
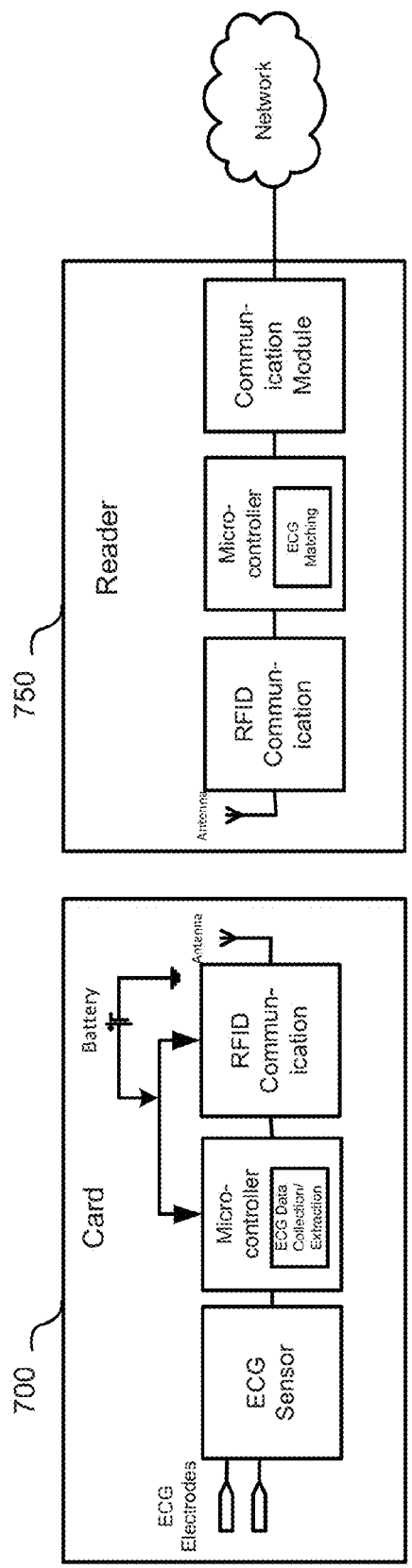
FIG. 7 shows contactless mode with on-reader authentication.

Communication with the reader is performed through an RFID channel as shown in FIG. 7. The ECG circuitry and on-card microcontroller on card 700 are powered through electromagnetic inductance from reader 750, a local battery or a combination of both methods.

Off-Reader—

In this approach, the ECG authentication process is done on the FC which returns the results of the authentication directly to the reader. This approach can be further divided into two modes, as described below.

Contact Mode with Off-Reader Authentication—

Figure 8:
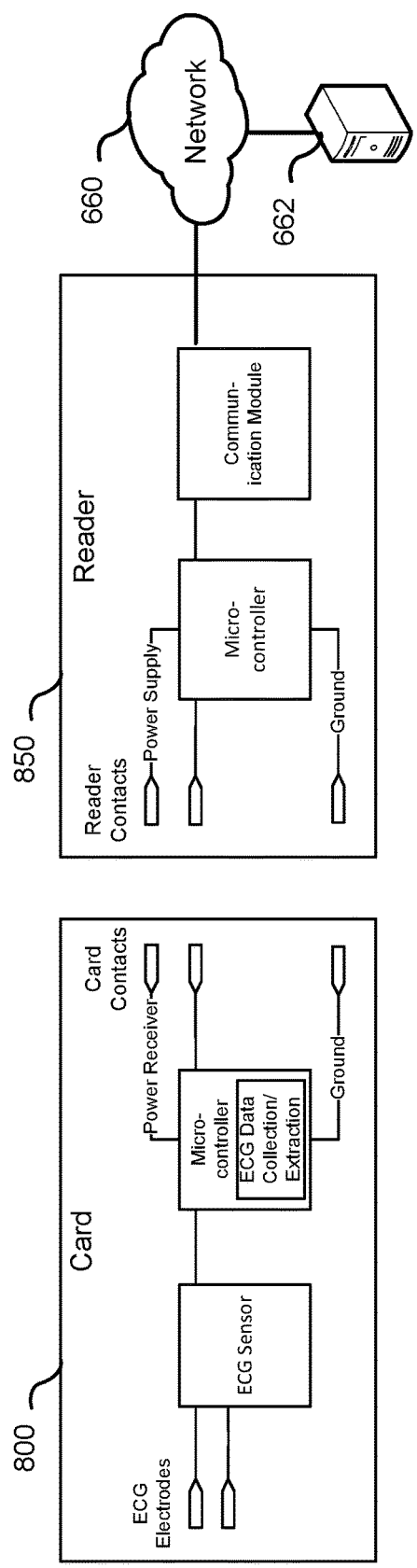
FIG. 8 shows contact mode in off-reader approach.

The components required for the Contact Mode with Off Reader Authentication are shown in FIG. 8. The ECG circuitry on the card 800 is directly powered by the reader 850. The microcontroller on the card 800 collects and extracts the relevant ECG data and it through a physical connection to the reader. The reader then sends the data to the server 662. The server 662 performs the authentication and returns the results of the latter process to the reader.

Contactless Mode with Off-Reader Authentication—

Figure 9:
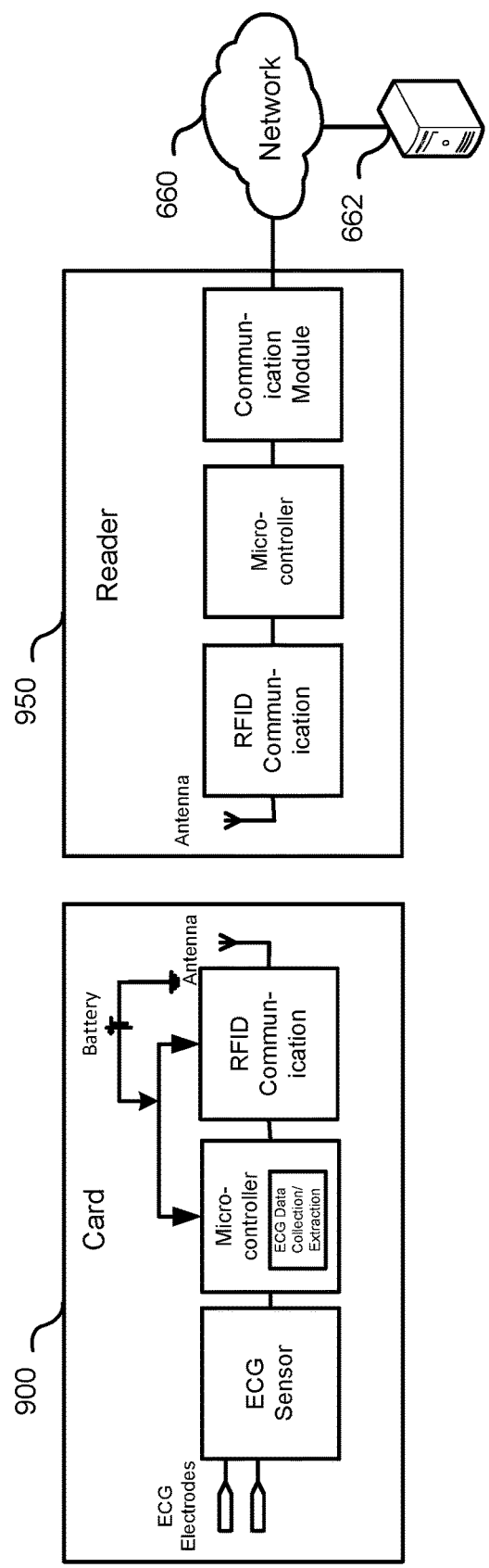
FIG. 9 shows contactless mode in off-reader approach.
Figure 10:
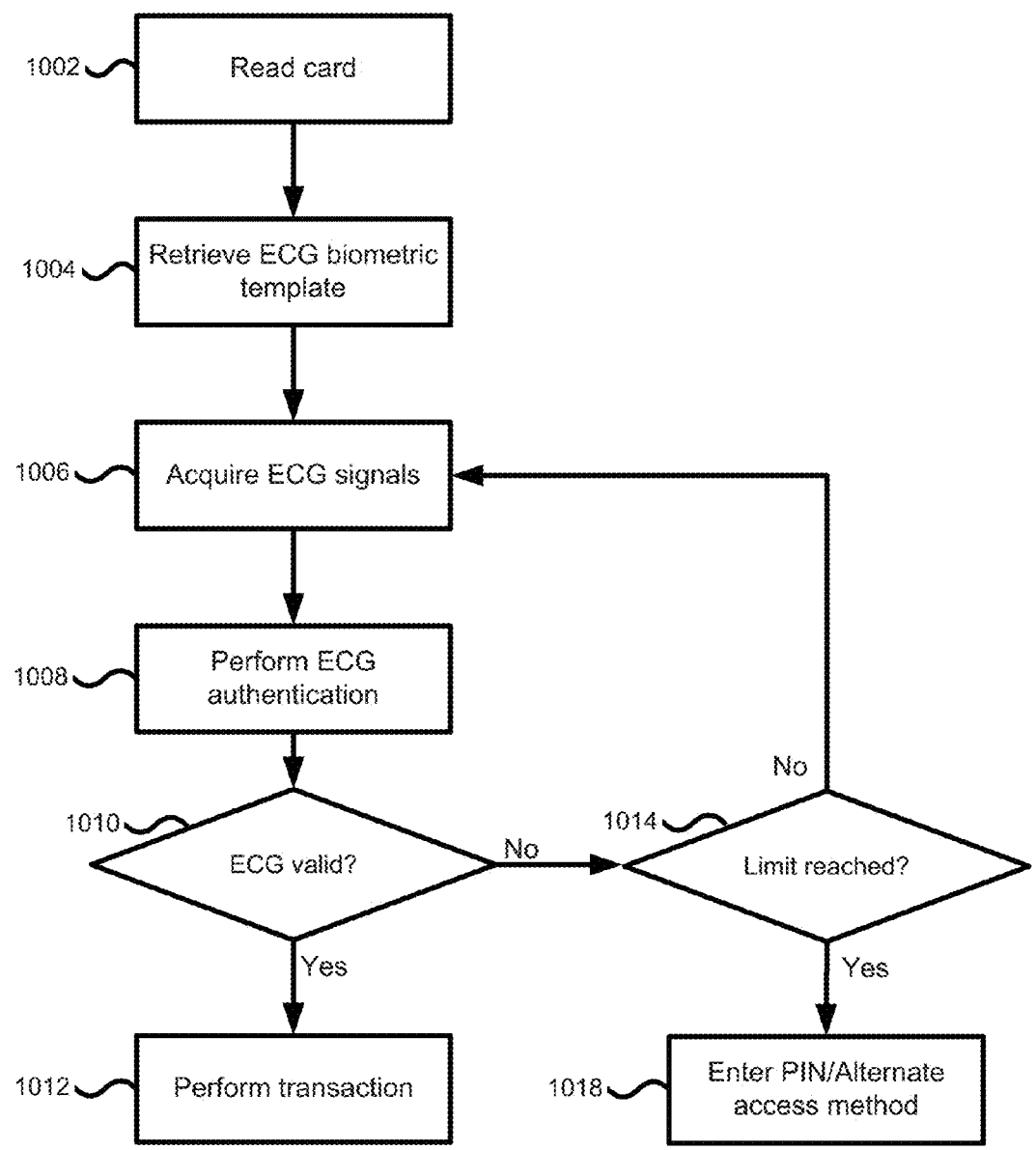
FIG. 10 shows a process for ECG authentication in cards.
Figure 11:
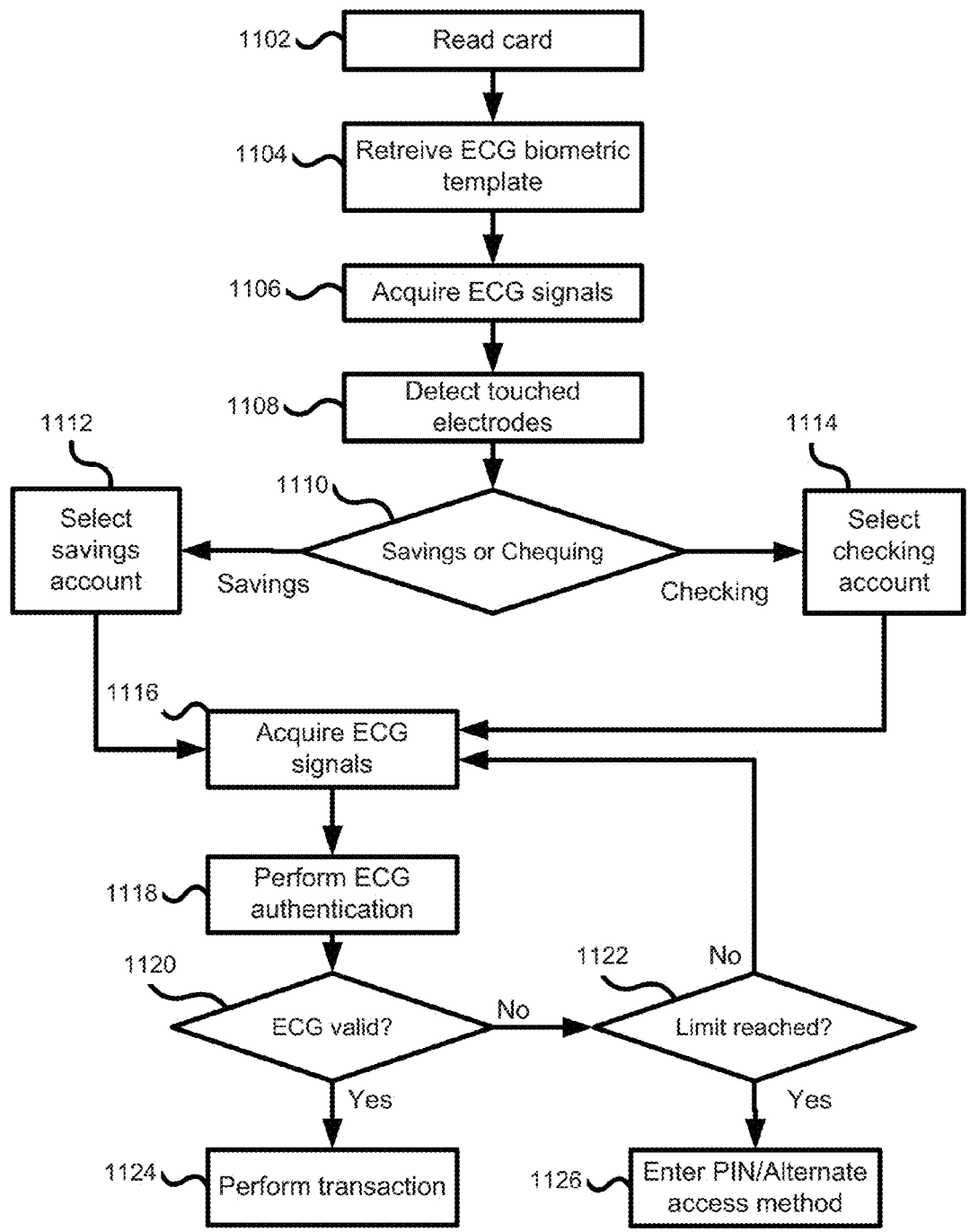
FIG. 11 shows ECG authentication in financial cards providing checking/savings account selection.

As shown in FIG. 9, the communication with the reader 950 is performed through a wireless channel. The ECG circuitry and on-card microcontroller on the card 900 are powered through electromagnetic inductance, a local battery, a combination of both methods or any other power supply mechanism.

In the case of the contact mode, the card must be inserted into a card reader. When inserted, the user must position two fingers from each hand onto the electrodes. In the case of the contactless mode, the user must touch the card's electrodes after placing the card in the radio range of the reader. Once the biometric device on the card collects enough ECG data, it can either send the whole signal or just the important features extracted from it to the reader.

The transferred ECG messages can be encrypted or unencrypted. It can contain specific ECG features or the entire ECG signal. For the first, the ECG feature extraction is performed on the card and for the second, the feature extraction occurs on the reader's computing apparatus. The set of extracted features is used in the authentication process.

In case the authentication process is successful, the transaction is allowed or access is granted. If the authentication process fails, then it is repeated. If a predetermined amount of attempts result in failure, then an alternative method of authentication can be employed (such as PIN based authentication). This procedure is shown in the method flow of FIG. 10. The card is read (1002) to determine user identification and a determined biometric template is retrieved (1004). ECG signals are acquired from the contacts (1006) and ECG authentication is performed (1008) by comparing a generated authentication template to the retrieved template. If the ECG signal is valid (YES at 1010) the transaction is performed (1012). If the ECG signal is not valid (NO at 1010) a retry limit is determined. If the retry limit is not reached (NO at 1014) ECG signals can be acquired again (1006) and validated. If the limit is reached (YES at 1014) a PIN can be requested (1018) for entry.

FCs equipped with fast access to checking or savings can be equipped with three or more electrodes. The reader senses the active electrodes in order to recognize the type of account to be used in the transaction. This process is shown in the method flow of FIG. 11. The card is read and identification of the user is determined (1102). An ECG biometric template associated with the user is retrieved (1104). An ECG signal is acquired from ECG contacts (1106). Depending on the electrodes that are contacted (1108) the type of account can be determined (1111). For example if the electrode associated with checking is in contact the checking account is selected for the transaction (1114). If the electrode for savings is touched the savings account is selected for the transaction (1112). The ECG signals may be continuously acquired (1106) or reacquired (1116) depending on the acquisition method utilized. ECG authentication can then be performed (1118) by generating an authentication template based upon the features determined from the ECG signal and comparing them to the retrieved template. If the ECG signal is valid (YES at 1120) the transaction is performed (1124). If the ECG signal is not valid (NO at 1120) a retry limit is determined. If the retry limit is not reached (NO at 1122) ECG signals can be acquired again (1116) and validated. If the limit is reached (YES at 1122) a PIN or alternate verification method can be requested (1126) for entry.

Figure 12:
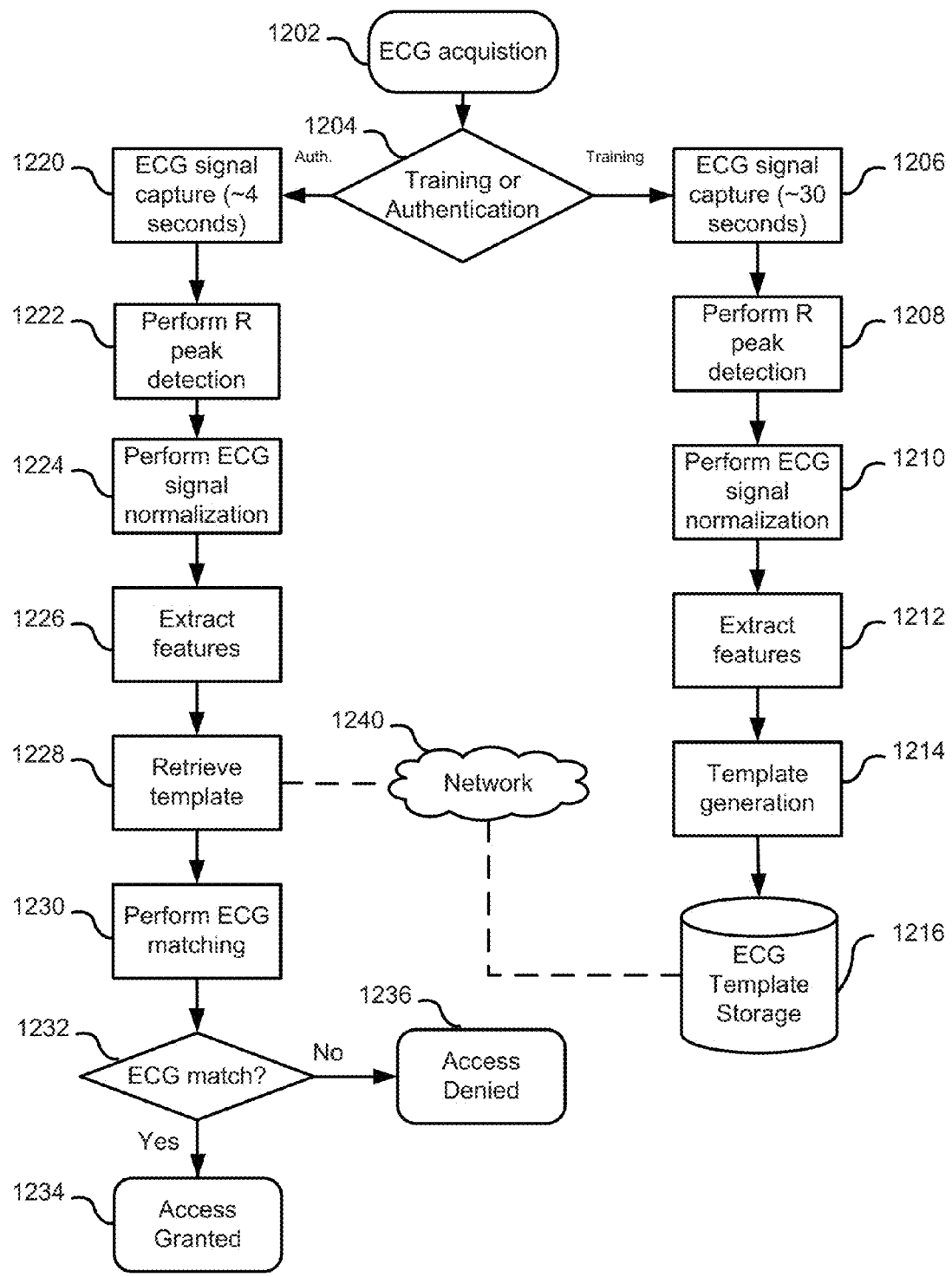
FIG. 12 shows ECG authentication process.

The ECG biometric process is composed of two stages: enrollment or training and authentication as shown in FIG. 12. During the enrollment stage, the BIT is generated. This process should be performed when the card is issued. It can also be repeated later at select readers to update or verify the BIT. The BIT generation is analogous to password creation/generation in traditional password based environments. To generate the BIT, the user must hold the ECG electrodes (on the card or a custom reader) for a predetermined period of time (until enough features are extracted for proper authentication).

Figure 13:
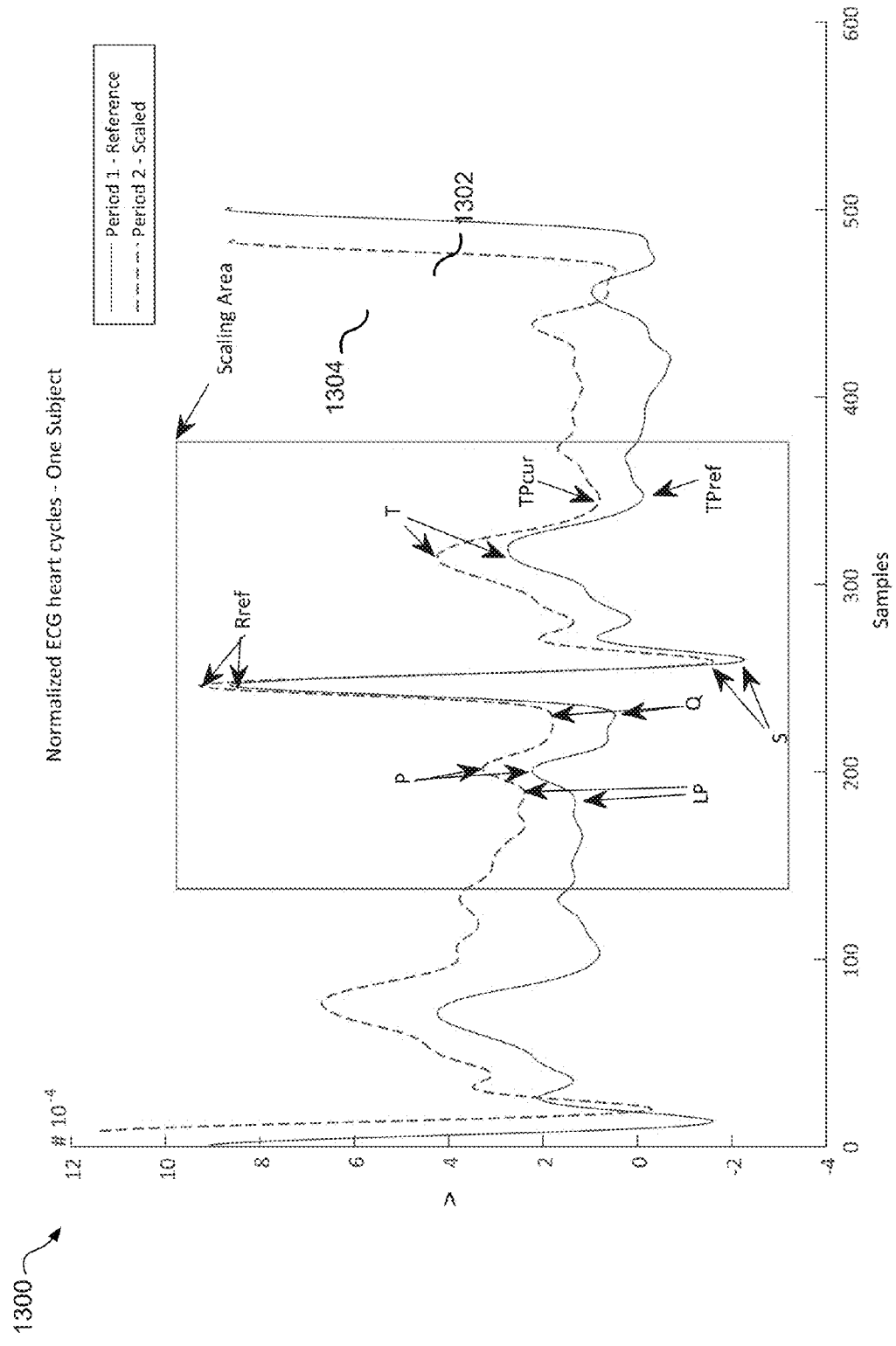
FIG. 13 shows normalization of ECG heart cycles by scaling.
Figure 14:
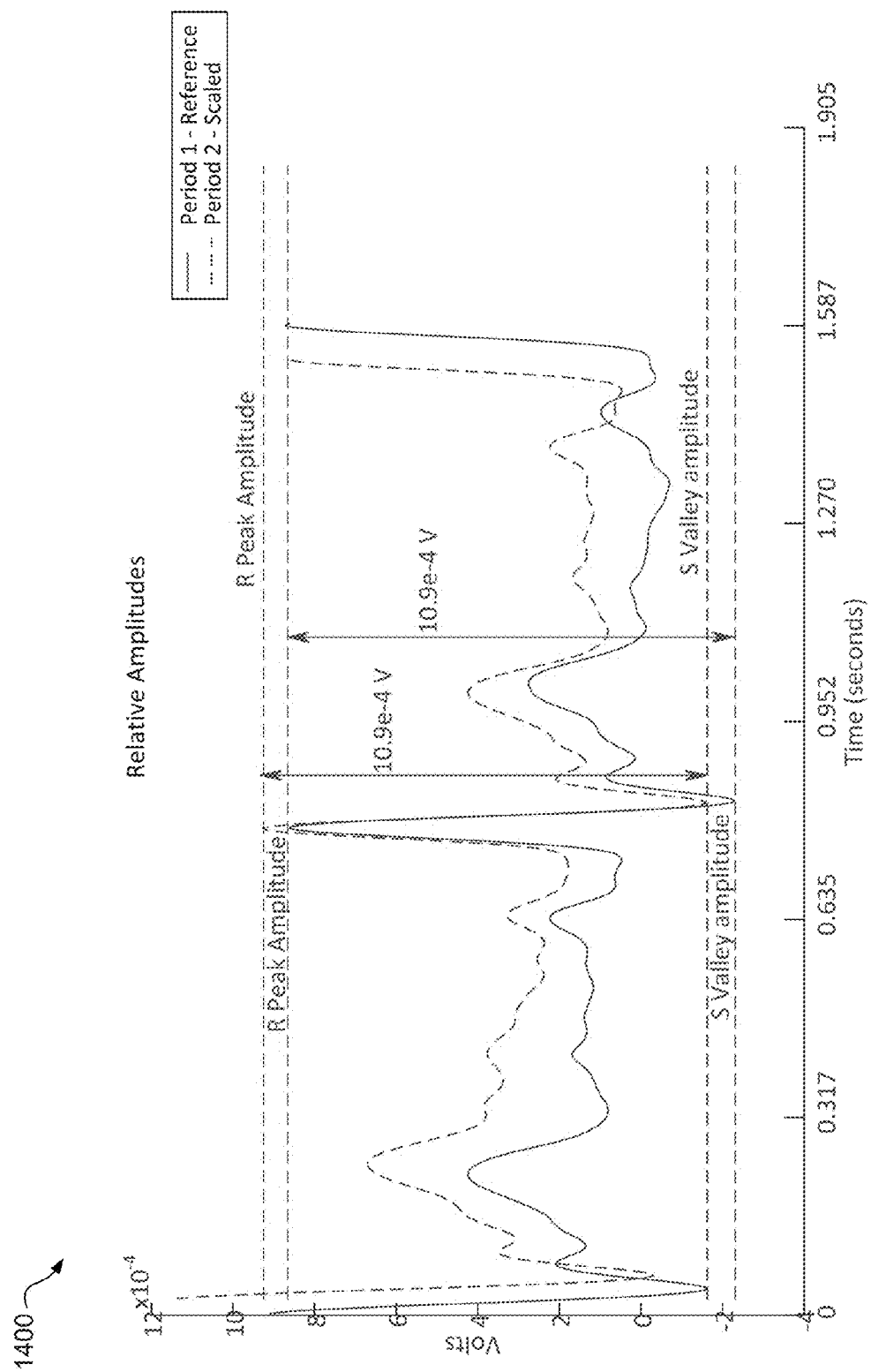
FIG. 14 shows that relative amplitudes remain the same for different ECG heart cycles.

The authentication stage is equivalent to the password inputting operation in traditional password based systems. To perform the authentication, the user must hold the ECG electrodes (1202) on the card for a predetermined period of time. In order to use an ECG signal for authentication, specific features from that signal need to be extracted. Typically, two types of features are extracted, time based features (i.e. time period between fiducial points) and amplitude based features (i.e. amplitude difference between fiducial points). Other types of features (e.g. frequency domain) can also be retrieved. During the enrolment sequence the ECG signal must be acquired for a prolonged period of time such as for example approximately 30 seconds (1206). R wave or peak detection is performed (1208) and the ECG signal is normalized (1210) by scaling the signal. This is done individually per heartbeat and two parts are taken as reference: the aligned point of R peaks ($R_{ref}$) and the median of all the indicies of the aligned TP valleys ($TP_{ref}$). Some of these features are affected by changes in the heart rate: therefore a normalization process is required before extracting them (in order to minimize the effect of heart rate change). For the normalization process, the ECG signal is expressed as a time series of data points. FIG. 13 shows an example of the normalization result in graph 1300 of the referenced signal 1302 to the scaled signal 1304. The ECG amplitude with respect to 0 volts changes constantly, but the amplitude relative to the R peak depends on the placement of the electrodes. Each point represents the amplitude of the ECG signal at a particular instant. Furthermore, an index is associated with each point. The index refers to the position of a point in the time series. For an ECG signal with N points, the indices range from 0 to N−1. Let a heart cycle be a subset of the ECG time series corresponding to a single heart beat (delimited by the TP and LP fiducial points). Therefore, an ECG time series representing B heart beats can be decomposed into B heart cycles. The normalization for time based features is performed by scaling the signal. The latter is performed as follows:

1) Divide the ECG signal into its composing heart cycles. This produces a time series for each heart cycle.

2) Align all the heart cycles by ensuring that their R peaks share the same index. The index at which all R peaks are aligned is called Rref.

3) Calculate the median of the indices of TP valleys from all heart cycles. This value will be referred to as TPref.

The medians of the TP valleys (Le. TPref) and the index of the aligned R peaks (i.e. Rref) are used to modify the index of all the points belonging to a heart cycle using Equation (1):

$$I_{new} = \frac{(I_{cur} - R_{ref}) \times (TP_{ref} - R_{ref})}{TP_{cur} - R_{ref}} + R_{ref} \quad (1)$$

Where, $I_{new}$ is the re-calculated index, $I_{cur}$ is the index that needs to be re-calculated, and $TP_{cur}$ is the index of the TP valley of the current heart cycle. In aligning the heartbeat the ECG heartbeats are shifted to be aligned around a reference point. Since R is the fiducial point less affected by noise (due to its distinguishable form), it is used to align all ECG heartbeats. Hence, all ECG heartbeats are shifted so that their start points, in the case the LP valley, overlap. Then with all the ECG heartbeats starting at the same point, the median of the indices values of the R peaks are calculated. This median value is the alignment point $R_{ref}$ that is used as reference to align the rest of the fiducial points.

FIG. 13 shows that relative amplitudes remain somewhat constant for successive ECG heart cycles.

Figure 15:
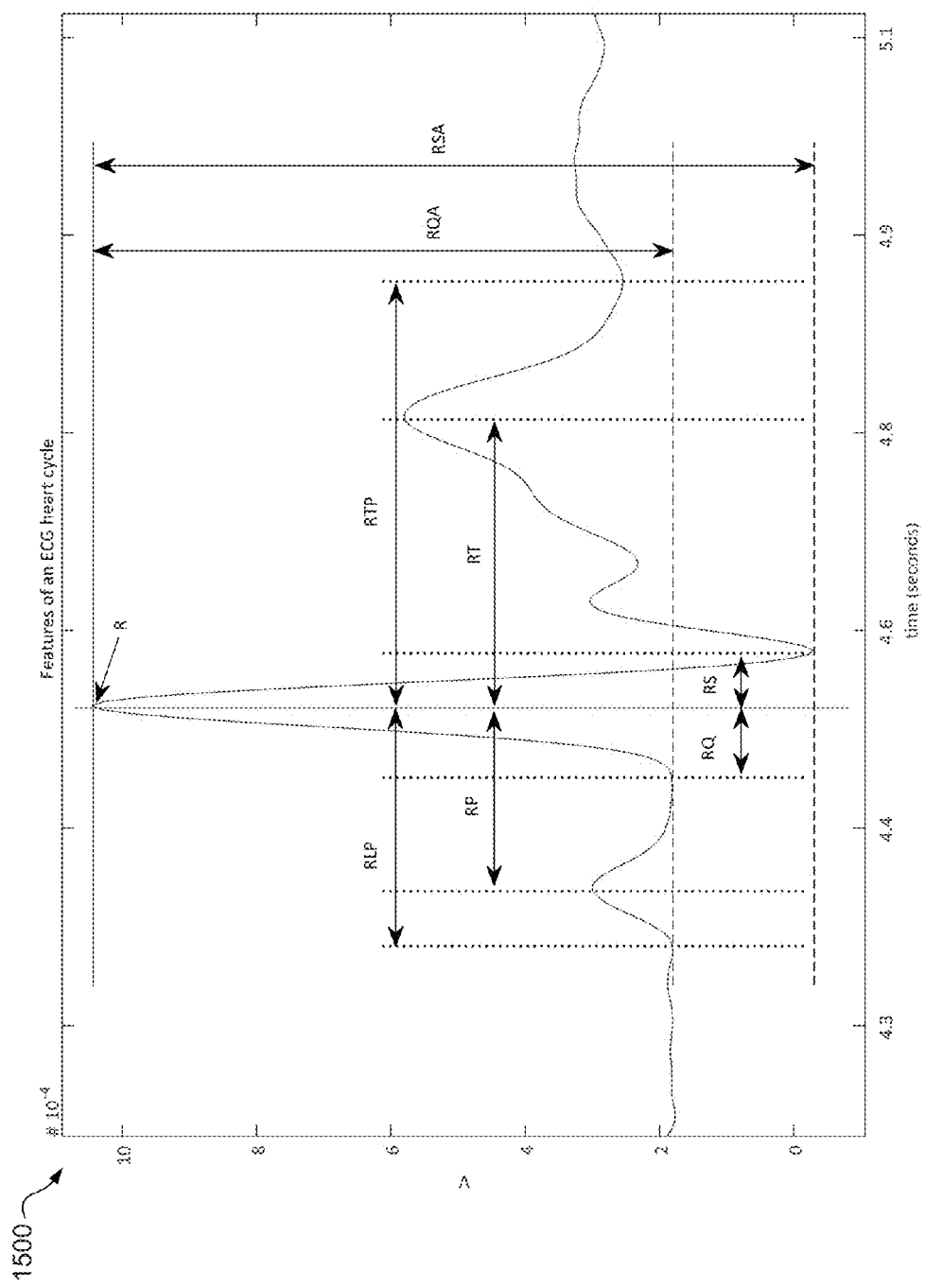
FIG. 15 shows extracted features from an ECG heart cycle.

A set of key features are extracted (1212) from the ECG signal. These features will be used to authenticate the card holder. FIG. 15 shows an example set of features that can be extracted from an ECG signal. The features shown in FIG. 15 are defined as follows:

RLP: time period between the beginning of the P wave and R peak

RP: time period between the peak of the P wave and R peak

RQ: time period between the Q wave and R peak

RS: time period between the R peak and S wave

RT: time period between the R peak and the peak of the T wave

RTP: time period between the R peak and the end of the T wave

RQA: voltage difference between the R peak and Q wave

RSA: voltage difference between the R peak and S wave

Additional features can be extracted from the signal. A time based feature is extracted by calculating the time period between a fiducial point and the R peak belonging to the same heart cycle. Also, an amplitude based feature is extracted by calculating the voltage difference between a fiducial point and the R peak belonging to the same heart cycle. From the features an ECG template can be generated for the user (1214) and stored (1216) either locally on the device or remotely.

During authentication (authentication at 1204) the ECG signal can be captured for a shorter period of time, for example approximately 4 seconds). R peak detection is performed (1222) and ECG signal normalization is performed as previously described (1224). Feature extraction is performed on the ECG signal and the template for the user is retrieved (1228) either via a network or from local storage. The ECG signal is then matched to the template (1230) by comparing ECG features data with an ECG Matching algorithm in order to perform authentication by comparing the collected features to the BIT. The algorithm produces an output indicating whether the input features match the BIT. This matching algorithm can use one or several classification methods, machine learning algorithms, or artificial intelligence techniques. If the template is matched (YES at 1232) access is granted, if the template does not match (NO at 1232) access is denied (1236).

Figure 16:
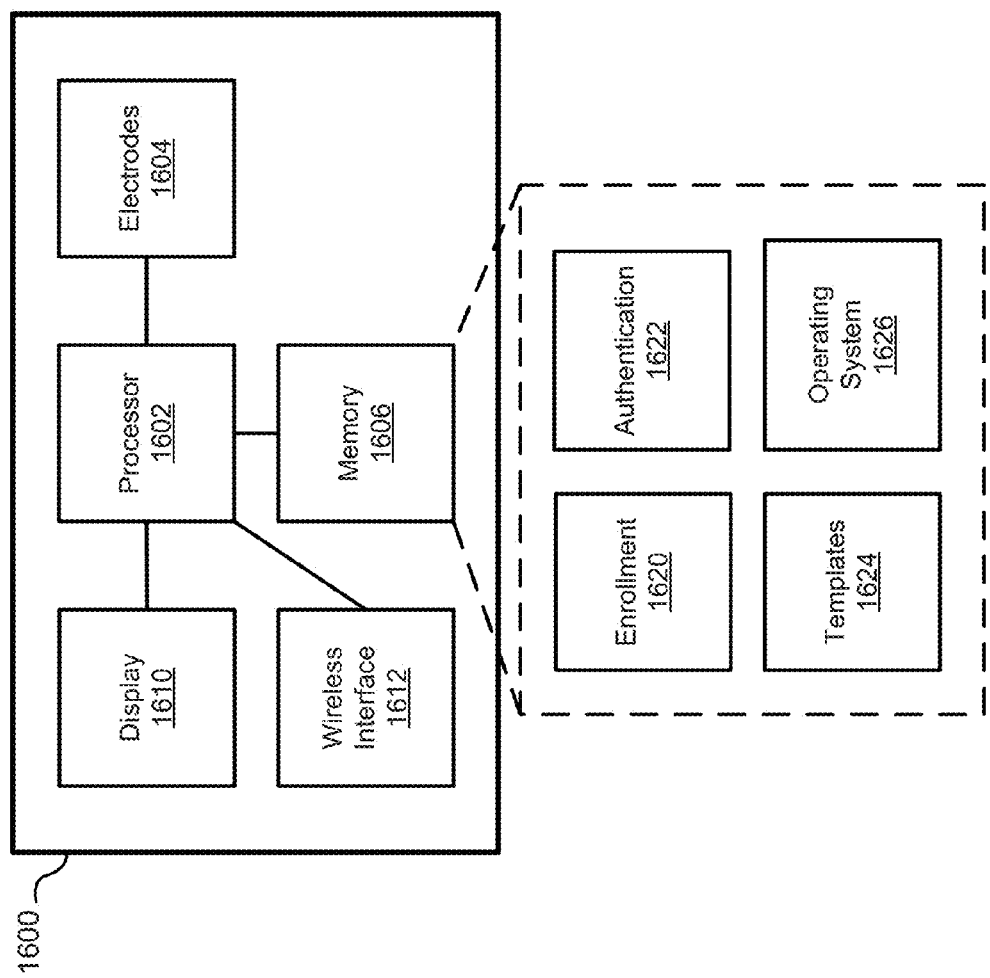
FIG. 16 shows a representation of a mobile device.

FIG. 16 shows a representation of a mobile device which has electrodes for using ECG authentication. The methods described in regards to card based authentication may be adapted for processing on a mobile device to provide authentication to access the device or features of the device. The mobile device 1600 contains a processor 1602 coupled to a memory 1606 containing instructions for executing the ECG authentication algorithm. Two or more electrodes 1604 are coupled to the processor 1602 and may be positioned on the mobile device 1600 to contact a user's fingers for generating an ECG signal. A display 1610 is coupled to the processor 1602 and may also provide touch input capability. A wireless interface 1612 is provided to communicate with a network for sending or receiving ECG signals, extracted features or templates. ECG data may be processed locally or may alternatively be transmitted through the network for processing. The memory 1606 contains instructions for execution by the processor 1602. The instructions can comprise one or more modules for providing enrollment 1620, enrollment templates 1624, authentication 1622 and an operating system 1626. The operating system 1626 can execute the ECG authentication process to restrict access to the mobile devices, or restrict access features of the device. The ECG authentication may unlock or decrypt the device or features of the device. The two or more electrode contacts may enable user to select features for access based upon which electrodes are contacted or the position on the electrodes. Alternatively the ECG signal may be provided by a peripheral device such as a wrist band or smart watch which can collect, relay or process ECG signals from the user.

Figure 17:
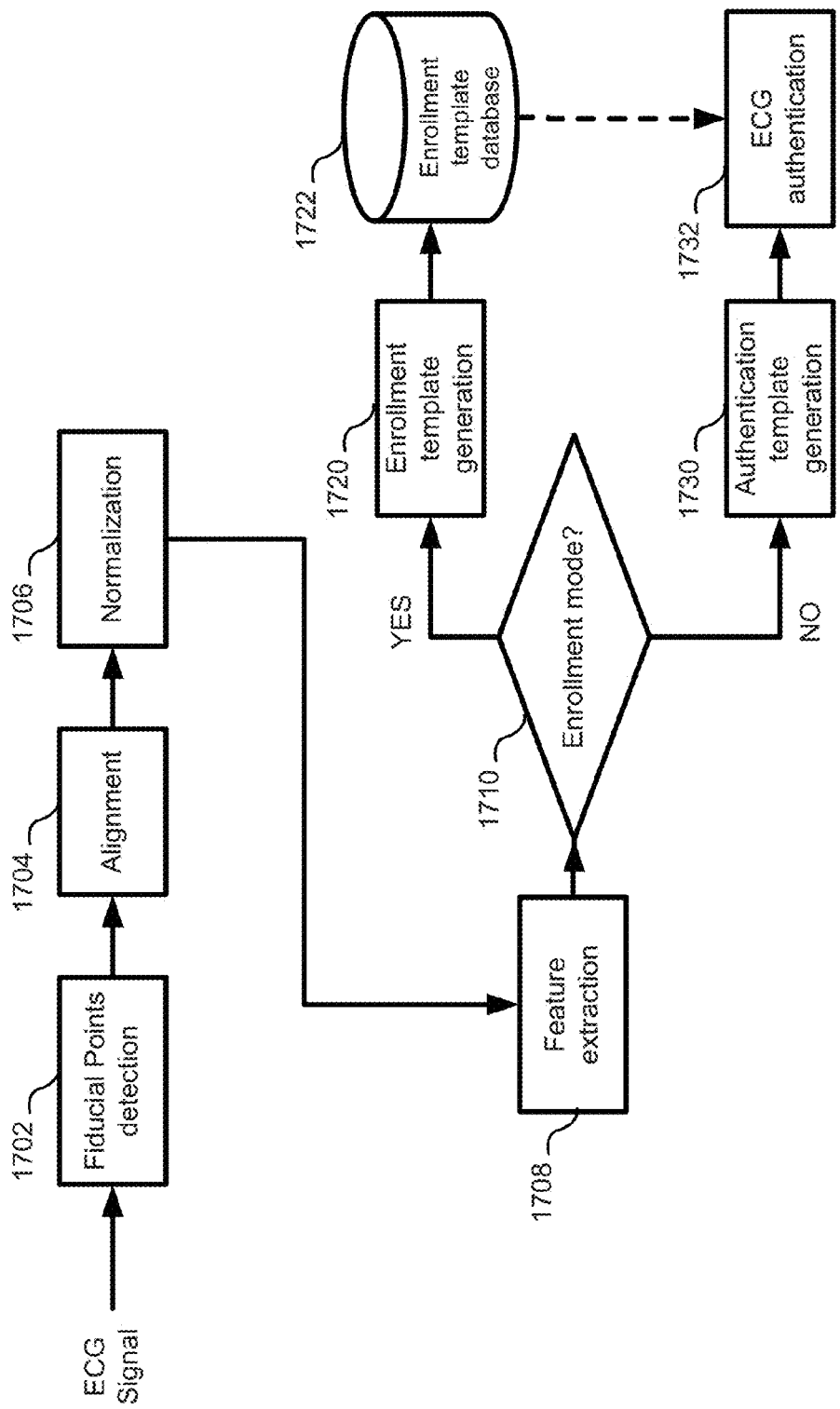
FIG. 17 shows a method of pre-processing before applying the ECG authentication.

FIG. 17 shows a method of pre-processing before applying the ECG authentication which can be used by a mobile device having ECG contact. An ECG signal is received and fiducial points are detected (1702). As previously described alignment is performed of heartbeats (1704), normalization of the heartbeats is then performed (1706), and feature extraction from the ECG signal is performed on the normalized heartbeat signal (1708). If the mobile device is in and enrollment mode (YES at 1710) enrollment template generation is performed (1720). The generated enrollment template is stored (1722) either locally or may be stored remotely. If the device is in not in the enrollment mode (NO at 1710) the device is locked or features disabled, an authentication template is generated (1730) and compared to the enrollment template (1722) to provide ECG authentication (1732). The device or features thereon can be unlocked based upon verification of the ECG of the user.

Each element in the embodiments of the present disclosure may be implemented as hardware, software/program, or any combination thereof. Software codes, either in its entirety or a part thereof, may be stored in a computer readable medium or memory (e.g., as a ROM, for example a non-volatile memory such as flash memory, CD ROM, DVD ROM, Blu-Ray™, a semiconductor ROM, USB, or a magnetic recording medium, for example a hard disk). The program may be in the form of source code, object code, a code intermediate source and object code such as partially compiled form, or in any other form.

It would be appreciated by one of ordinary skill in the art that the system and components shown in FIGS. 1-17 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

The invention claimed is:

1. A method of security authentication, the method comprising:
   receiving electrocardiogram (ECG) signals from contact electrodes;
   transferring ECG signals to a processor;
   extracting features from ECG data of the ECG signal by the processor;
   verifying ECG data against stored biometric information template (BIT) associated with a user; and
   providing access to the user based upon confirmed ECG data;

wherein the ECG data is normalized by:
dividing the ECG data into its composing heart cycles;
aligning all the heart cycles by ensuring that their R peaks share a same index wherein the index at which all R peaks are aligned is referred to as Rref and there the calculated median of the indicies is referred to as TPref; and
calculating a median of indices of TP valleys from all heart cycles wherein median is an alignment point $R_{ref}$ that is used as a reference to align fiducial points of the ECG data and medians of TP valleys, TPref and Rref are used to modify the index of all the points belonging to a heart cycle
where alignment is performed by:

$$I_{new} = \frac{(I_{cur} - R_{ref}) \times (TP_{ref} - R_{ref})}{TP_{cur} - R_{ref}} + R_{ref}$$

where, $I_{new}$ is a re-calculated index, $I_{cur}$ is an index that needs to be re-calculated, and $TP_{cur}$ is the index of the TP valley of a current heart cycle.

2. The method of claim 1 wherein comparing the ECG data against stored BIT comprises comparing the extracted features to features stored in the BIT for an associated user.

3. The method of claim 2 wherein the extracted features are time based or amplitude based feature of the ECG.

4. The method of claim 3 wherein the extracted features of the ECG are selected from the group consisting of:
RLP: time period between a beginning of a P wave and R peak;
RP: time period between a peak of the P wave and R peak;
RQ: time period between a Q wave and R peak;
RS: time period between a R peak and S wave;
RT: time period between a R peak and a peak of a T wave;
RTP: time period between a R peak and a end of the T wave;
RQA: voltage difference between a R peak and Q wave; and
RSA: voltage difference between a R peak and S wave.

5. The method of claim 1 wherein aligning heartbeats the ECG heartbeats are shifted to be aligned around a reference point.

6. The method of claim 5 wherein R peak of the ECG is a fiducial point used to align all ECG heartbeats.

7. The method of claim 1 wherein verifying ECG data against stored BIT comprising performing matching of the features between the extracted feature data to features defined in the BIT.

8. The method of claim 1 further comprising an enrollment mode prior to performing security authentication wherein the enrollment mode method comprises:
receiving enrollment ECG data;
detecting fiducial points in the enrollment ECG data for a plurality of heartbeats;
performing alignment of the plurality of heartbeats
extracting features of the enrollment ECG data the plurality of heartbeats; and
generating an BIT from the extracted features.

9. The method of claim 1 wherein the ECG contact electrodes are on a card for providing access to an associated account or location.

10. The method of claim 1 wherein the ECG contact electrodes are on a mobile device wherein access is provided to an operating system or feature of the mobile device.

11. An electrocardiogram (ECG) authentication device comprising:
at least two electrodes;
a microcontroller coupled to the electrodes for processing an ECG signal received from the electrodes; and
memory containing instructions for processing the ECG signal by the microcontroller to extract features from ECG data which is verified against a stored biometric information template (BIT) whereby access is granted to the device or a computing system interfaced with the ECG device based upon comparison of the ECG data to the BIT wherein the BIT is associated with a user of the ECG device;
wherein the ECG data is normalized by:
dividing the ECG data into its composing heart cycles;
aligning all the heart cycles by ensuring that their R peaks share a same index wherein the index at which all R peaks are aligned is referred to as Rref and there the calculated median of the indicies is referred to as TPref; and
calculating a median of indices of TP valleys from all heart cycles wherein median is an alignment point Rref that is used as a reference to align fiducial points of the ECG data and medians of TP valleys, TPref and Rref are used to modify the index of all the points belonging to a heart cycle
where alignment is performed by:

$$I_{new} = \frac{(I_{cur} - R_{ref}) \times (TP_{ref} - R_{ref})}{TP_{cur} - R_{ref}} + R_{ref}$$

where, $I_{new}$ is a re-calculated index, $I_{cur}$ is an index that needs to be re-calculated, and $TP_{cur}$ is the index of the TP valley of a current heart cycle.

12. The ECG authentication device of claim 11 wherein the ECG authentication device is a card having the least two electrodes received and ECG by two finger contact.

13. The ECG authentication device of claim 11 wherein the BIT uses time based feature and amplitude based features.

14. The ECG authentication device of claim 11 wherein comparing the ECG data against stored BIT comprises comparing the extracted features to features stored in the BIT for an associated user.

15. The ECG authentication device of claim 14 wherein the extracted features are time based or amplitude based feature of the ECG.

16. The ECG authentication device of claim 15 wherein the extracted features of the ECG are selected from the group consisting of:
RLP: time period between a beginning of a P wave and R peak;
RP: time period between a peak of the P wave and R peak;
RQ: time period between a Q wave and R peak;
RS: time period between a R peak and S wave;
RT: time period between a R peak and a peak of a T wave;
RTP: time period between a R peak and a end of the T wave;
RQA: voltage difference between a R peak and Q wave; and
RSA: voltage difference between a R peak and S wave.

17. The ECG authentication device of claim 11 wherein the ECG is normalized by:

dividing the ECG data into its composing heart cycles;
aligning all the heart cycles by ensuring that their R peaks share a same index; and
calculating a median of indices of TP valleys from all heart cycles.

* * * * *